(12) United States Patent
Dawoodjee

(10) Patent No.: US 11,969,304 B1
(45) Date of Patent: Apr. 30, 2024

(54) INSTRUMENT BRIDGE TO ELEVATE AND PROTECT THE TIPS OF SURGICAL INSTRUMENTS PLACED IN A SURGICAL INSTRUMENT TRAY

(71) Applicant: John Dawoodjee, Canoga Park, CA (US)

(72) Inventor: John Dawoodjee, Canoga Park, CA (US)

( * ) Notice: Subject to any disclaimer, the term of this patent is extended or adjusted under 35 U.S.C. 154(b) by 23 days.

(21) Appl. No.: 17/898,655

(22) Filed: Aug. 30, 2022

Related U.S. Application Data

(60) Provisional application No. 63/238,613, filed on Aug. 30, 2021.

(51) Int. Cl.
*A61B 90/50* (2016.01)
*A47F 5/01* (2006.01)
*A47F 7/00* (2006.01)
*A61B 17/3201* (2006.01)

(52) U.S. Cl.
CPC ............... *A61B 90/50* (2016.02); *A47F 5/01* (2013.01); *A47F 7/00* (2013.01); *A47F 7/0021* (2013.01); *A61B 17/3201* (2013.01)

(58) Field of Classification Search
CPC . A61B 90/50; A61B 17/3201; A61B 19/0256; A61B 2019/0258; A61B 19/26; A61B 2019/0259; A47F 5/01; A47F 7/00; A47F 7/0021
USPC ............................... 211/85.13; 206/363, 370
See application file for complete search history.

(56) References Cited

U.S. PATENT DOCUMENTS

| | | | | | |
|---|---|---|---|---|---|
| 287,745 | A | * | 10/1883 | Warne | A45F 5/02 24/3.12 |
| 530,014 | A | * | 11/1894 | Chandler | A45F 5/02 24/3.1 |
| D28,771 | S | * | 5/1898 | Mills | 211/1 |
| 742,710 | A | * | 10/1903 | Moore | A45F 5/02 24/3.1 |
| 800,535 | A | * | 9/1905 | Armel | A44C 1/00 24/13 |
| 938,025 | A | * | 10/1909 | Smoot | D06F 55/00 D19/83 |
| 2,286,831 | A | * | 6/1942 | Ressinger | A47F 5/01 D6/672 |
| 3,035,582 | A | * | 5/1962 | Seiger | A61B 17/28 600/218 |
| D194,597 | S | * | 2/1963 | Bryant | D8/395 |

(Continued)

*Primary Examiner* — Devin K Barnett
(74) *Attorney, Agent, or Firm* — Plager Schack LLP; Mark H. Plager; Stephen Hallberg

(57) ABSTRACT

An instrument bridge to elevate and protect the tips of surgical instruments placed in a surgical instrument tray is disclosed. The instrument bridge provides a rigid stand that is configured to elevate and protect the tips of surgical instruments secured onto a sterilization/instrument stringer or loosely placed into the surgical instrument tray with their tips elevated and placed onto the instrument bridge. The instrument bridge is a rigid medical instrument stand that is made of either stainless steel or plastic material. The stainless steel instrument bridge is reusable, works with all types and lengths of instruments, and can be sterilized. The plastic instrument bridge is a single-use medical instrument stand that is disposable, can be sterilized and works with all types and lengths of instruments.

11 Claims, 2 Drawing Sheets

(56) References Cited

U.S. PATENT DOCUMENTS

| | | | | |
|---|---|---|---|---|
| 3,693,808 A | * | 9/1972 | Rauch | A47F 5/13 |
| | | | | 211/195 |
| 3,925,014 A | * | 12/1975 | Langdon | A61L 2/26 |
| | | | | 206/370 |
| 4,043,754 A | * | 8/1977 | Sklar | A61L 2/26 |
| | | | | 248/222.12 |
| 4,142,632 A | * | 3/1979 | Sandel | A61B 50/20 |
| | | | | 206/478 |
| 4,229,420 A | * | 10/1980 | Smith | A61B 50/22 |
| | | | | 606/1 |
| 4,342,391 A | * | 8/1982 | Schainholz | A61B 50/20 |
| | | | | 206/370 |
| 4,385,692 A | * | 5/1983 | Eldridge, Jr. | A61B 50/30 |
| | | | | 206/363 |
| 4,506,787 A | * | 3/1985 | Bruso | A61B 50/20 |
| | | | | 206/363 |
| 4,512,466 A | * | 4/1985 | Delang | A61B 50/20 |
| | | | | 206/370 |
| 4,643,303 A | * | 2/1987 | Arp | A61L 2/26 |
| | | | | 206/370 |
| D300,804 S | * | 4/1989 | Myers | D34/5 |
| 4,821,985 A | * | 4/1989 | DeMatteis | A47F 13/085 |
| | | | | 211/12 |
| 4,865,821 A | * | 9/1989 | Langdon | A61B 50/22 |
| | | | | 422/561 |
| 5,137,151 A | * | 8/1992 | Choate | A61B 50/20 |
| | | | | 206/370 |
| 5,435,295 A | * | 7/1995 | Gerrard | F24B 1/193 |
| | | | | 126/541 |
| 5,501,653 A | * | 3/1996 | Chin | A61B 90/50 |
| | | | | 606/198 |
| 5,743,450 A | * | 4/1998 | Plate | A45F 5/00 |
| | | | | 224/267 |
| 6,155,439 A | * | 12/2000 | Draughn | A61B 50/22 |
| | | | | 211/85.13 |
| 6,230,888 B1 | * | 5/2001 | Frieze | A61B 50/22 |
| | | | | 206/370 |
| D488,865 S | * | 4/2004 | Todia | D24/128 |
| D619,704 S | * | 7/2010 | Foy | D24/128 |
| 7,950,537 B1 | * | 5/2011 | Goodman | A47B 57/581 |
| | | | | 211/184 |
| D669,635 S | * | 10/2012 | Goodman | D28/38 |
| D714,081 S | * | 9/2014 | Simone | A47G 33/004 |
| | | | | D6/675.4 |
| 8,925,157 B2 | * | 1/2015 | O'Daniel | B42F 1/08 |
| | | | | 24/DIG. 10 |
| D731,877 S | * | 6/2015 | Hanson | D8/370 |
| 9,156,571 B2 | * | 10/2015 | Ramkhelawan | A61B 50/22 |
| D875,516 S | * | 2/2020 | Mao | D8/394 |
| D968,596 S | * | 11/2022 | Smith | D24/128 |
| D981,209 S | * | 3/2023 | Sun | D8/333 |
| 2001/0035384 A1 | * | 11/2001 | Davis | A61B 50/20 |
| | | | | 206/370 |
| 2005/0040066 A1 | * | 2/2005 | Pulsifer | A61B 50/24 |
| | | | | 206/438 |
| 2005/0061696 A1 | * | 3/2005 | Swank | A61B 50/20 |
| | | | | 206/363 |
| 2007/0075210 A1 | * | 4/2007 | Yang | G09F 1/10 |
| | | | | 248/456 |
| 2007/0205171 A1 | * | 9/2007 | Iwata | A47G 19/30 |
| | | | | 211/181.1 |
| 2010/0298774 A1 | * | 11/2010 | Igov | A61F 17/29 |
| | | | | 604/164.01 |
| 2012/0199703 A1 | * | 8/2012 | Taylor | A61B 90/50 |
| | | | | 248/70 |
| 2012/0234781 A1 | * | 9/2012 | Cogliano | B25H 3/06 |
| | | | | 211/85.13 |
| 2013/0074450 A1 | * | 3/2013 | Higham | A61B 50/30 |
| | | | | 206/370 |
| 2013/0105346 A1 | * | 5/2013 | Ramkhelawan | A61B 50/33 |
| | | | | 206/370 |
| 2014/0001067 A1 | * | 1/2014 | Gitman | A61B 50/33 |
| | | | | 206/363 |
| 2014/0318085 A1 | * | 10/2014 | Sill | A47F 5/0006 |
| | | | | 211/49.1 |
| 2018/0056500 A1 | * | 3/2018 | Reeves | F16M 13/00 |
| 2018/0369485 A1 | * | 12/2018 | Yalisove | A61M 5/008 |
| 2022/0296749 A1 | * | 9/2022 | Jun | A61L 2/26 |
| 2023/0052337 A1 | * | 2/2023 | Carlo, III | A61B 17/1633 |
| 2023/0211628 A1 | * | 7/2023 | Bouda | B43M 99/001 |
| | | | | 446/359 |

\* cited by examiner

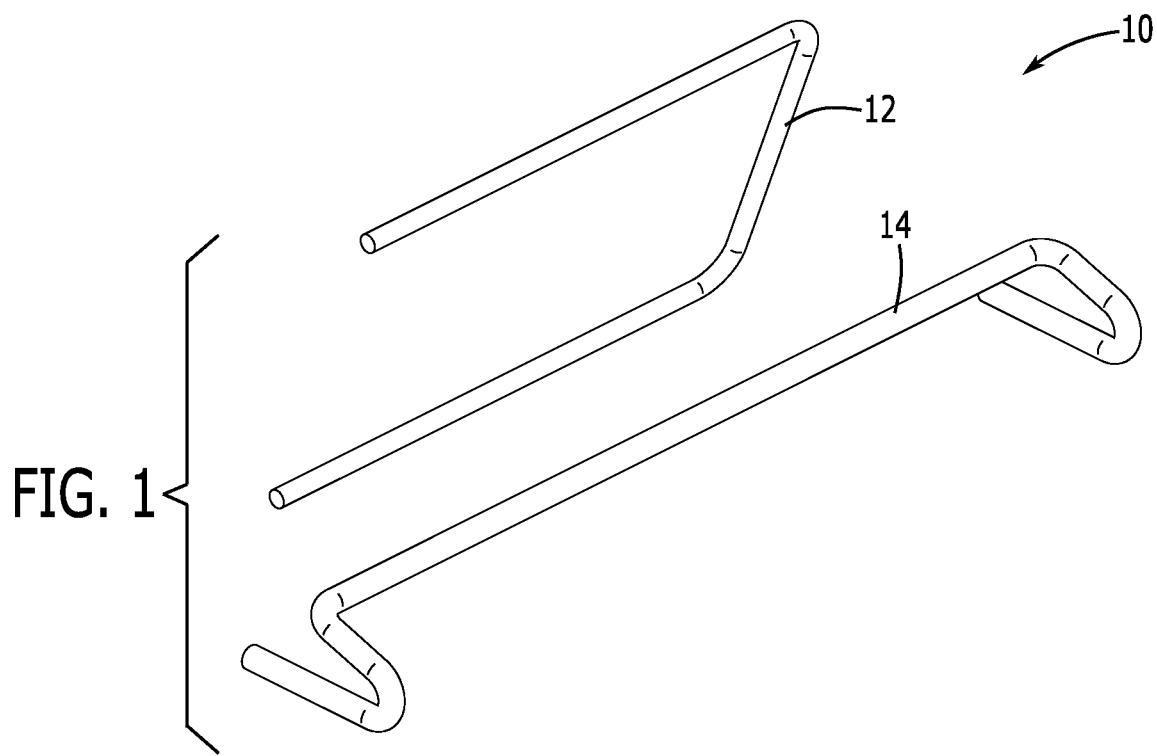
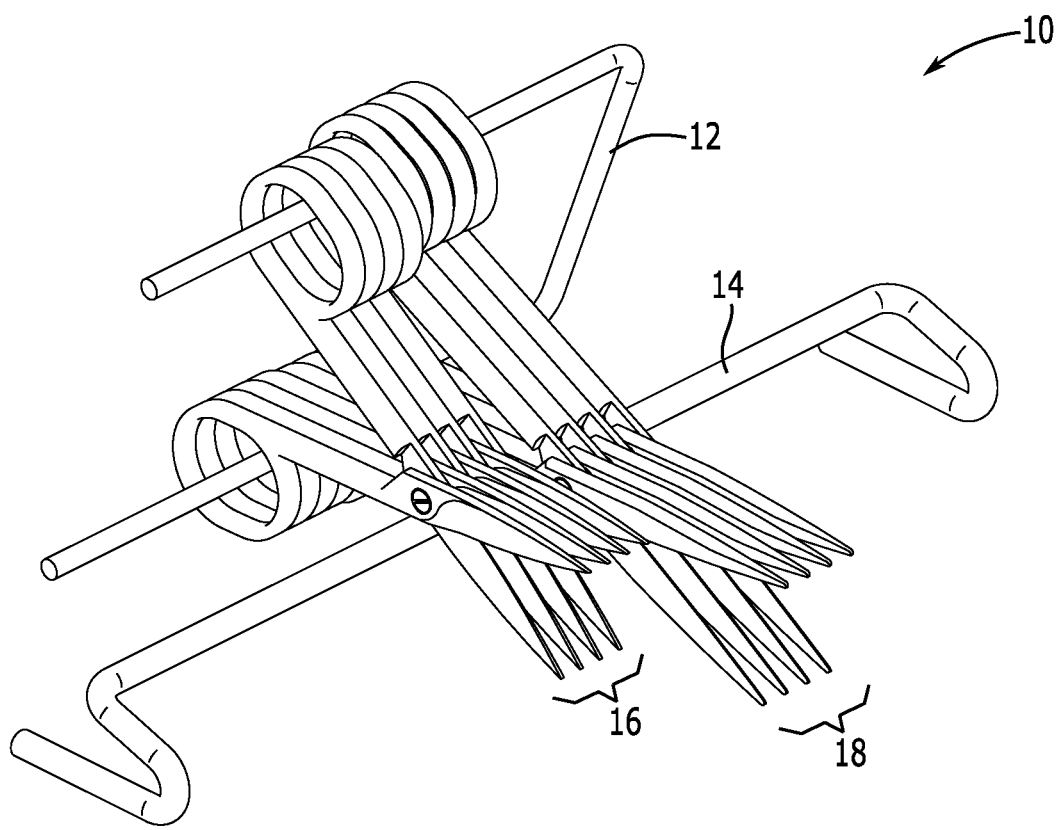

INSTRUMENT BRIDGE TO ELEVATE AND PROTECT THE TIPS OF SURGICAL INSTRUMENTS PLACED IN A SURGICAL INSTRUMENT TRAY

CLAIM OF BENEFIT TO PRIOR APPLICATION

This application claims benefit to U.S. Provisional Patent Application 63/238,613, entitled "AN INSTRUMENT BRIDGE TO ELEVATE AND PROTECT THE TIPS OF SURGICAL INSTRUMENTS PLACED IN A SURGICAL INSTRUMENT TRAY," filed Aug. 30, 2021. The U.S. Provisional Patent Application 63/238,613 is incorporated herein by reference.

BACKGROUND

Embodiments of the invention described in this specification relate generally to surgical devices, and more particularly, to an instrument bridge to elevate and protect the tips of both surgical instruments secured onto a sterilization/instrument stringer placed in a surgical instrument tray and surgical instruments loosely placed into the surgical instrument tray with the tips placed on the instrument bridge.

The sharp and delicate tips of surgical instruments, when the instruments are secured onto a sterilization/instrument stringer and placed in a surgical instrument tray or loosely placed in a surgical instrument tray, can catch or hang up on the perforated bottom of the surgical instrument tray and break, bend, or crack.

To reduce the risk of damage by contact with the perforated bottom of the tray, cloth towels or other fabrics or materials are often used to elevate the instrument tips. However, the use of cloth towels or other fabrics or materials can result in lint or other fabric residue on the instruments. Furthermore, the instrument tips can catch on the material and damage the tips.

Therefore, what is needed is a better way to protect the tips of surgical instruments placed on sterilization/instrument stringers or loosely placed in surgical instrument trays.

BRIEF DESCRIPTION

An instrument bridge to elevate and protect the tips of both surgical instruments secured onto a sterilization/instrument stringer placed in a surgical instrument tray and surgical instruments loosely placed into the surgical instrument tray with the tips placed on the instrument bridge is disclosed. In some embodiments, the instrument bridge provides a rigid stand that is configured to elevate and protect the tips of surgical instruments secured onto the sterilization/instrument stringer placed in the surgical instrument tray or loosely placed into the surgical instrument tray with their tips elevated and placed onto the instrument bridge. In some embodiments, the instrument bridge is manufactured in a plurality of different sizes that each fit different sized surgical instrument trays. In this way, there is nothing for the instruments to catch on, there is no lint residue or cross-contamination, and multiple sizes can accommodate most surgical instrument trays. In some embodiments, the instrument bridge is a rigid medical instrument stand that is made of stainless steel, is reusable, works with all types and lengths of instruments, and can be sterilized. In some embodiments, the instrument bridge is a single-use medical instrument stand that is made of a plastic material, is disposable, can be sterilized and works with all types and lengths of instruments.

In some embodiments, the instrument bridge comprises an elongated instrument elevation bar and instrument bridge feet that are inseparably connected to the ends of the elongated instrument elevation bar, making a single component surgical instrument bridge. In some embodiments, the instrument bridge feet extend out from opposite ends of the elongated instrument elevation bar and raise the elongated instrument elevation bar above a surface platform in a horizontal orientation to stabilize the surgical instrument bridge when placed on the surface platform. In some embodiments, the elongated instrument elevation bar is configured to elevate a distal end (also referred to as the "tip end") of a surgical instrument. In some embodiments, the elongated instrument elevation bar is configured to elevate the distal end of the surgical instrument when a proximal end (also referred to as the "opposite end" or "handle end") of the surgical instrument is secured by an instrument stringer. In some embodiments, the elongated instrument elevation bar is configured to elevate the distal end of the surgical instrument when the proximal end of the surgical instrument lays on (or touches) a surface of a surgical instrument tray. In some embodiments, the surgical instrument bridge is approximately a size of the size of a surgical instrument tray on which the surgical instrument bridge is intended for use. In some embodiments, the surgical instrument bridge is approximately a size that is sufficient to support a particular type of surgical instrument. In some embodiments, the surgical instrument bridge is approximately a size that is sufficient to support a plurality of surgical instruments of different sizes.

In some embodiments, the particular type of surgical instrument comprises surgical scissors. In some embodiments, the particular type of surgical instrument comprises any surgical instrument from a plurality of surgical instruments with distal and proximal ends. In some embodiments, the surgical instrument bridge elevates the distal ends of both small size surgical scissors and large sized surgical scissors. In some embodiments, the surgical instrument bridge is configured to elevate the distal ends of surgical scissors of any size. In some embodiments, finger holes at a proximal end of the surgical scissors are looped onto an instrument stringer positioned nearby the surgical instrument bridge.

The preceding Summary is intended to serve as a brief introduction to some embodiments of the invention. It is not meant to be an introduction or overview of all inventive subject matter disclosed in this specification. The Detailed Description that follows and the Drawings that are referred to in the Detailed Description will further describe the embodiments described in the Summary as well as other embodiments. Accordingly, to understand all the embodiments described by this document, a full review of the Summary, Detailed Description, and Drawings is needed. Moreover, the claimed subject matters are not to be limited by the illustrative details in the Summary, Detailed Description, and Drawings, but rather are to be defined by the appended claims, because the claimed subject matter can be embodied in other specific forms without departing from the spirit of the subject matter.

BRIEF DESCRIPTION OF THE DRAWINGS

Having described the invention in general terms, reference is now made to the accompanying drawings, which are not necessarily drawn to scale, and wherein:

FIG. 1 conceptually illustrates an exploded perspective view of an instrument bridge designed to elevate and protect tips of surgical instruments in some embodiments.

FIG. 2 conceptually illustrates a perspective view of the instrument bridge with several surgical instruments on an instrument stringer with tips of the surgical instruments elevated by the instrument bridge.

DETAILED DESCRIPTION

Figure 3:
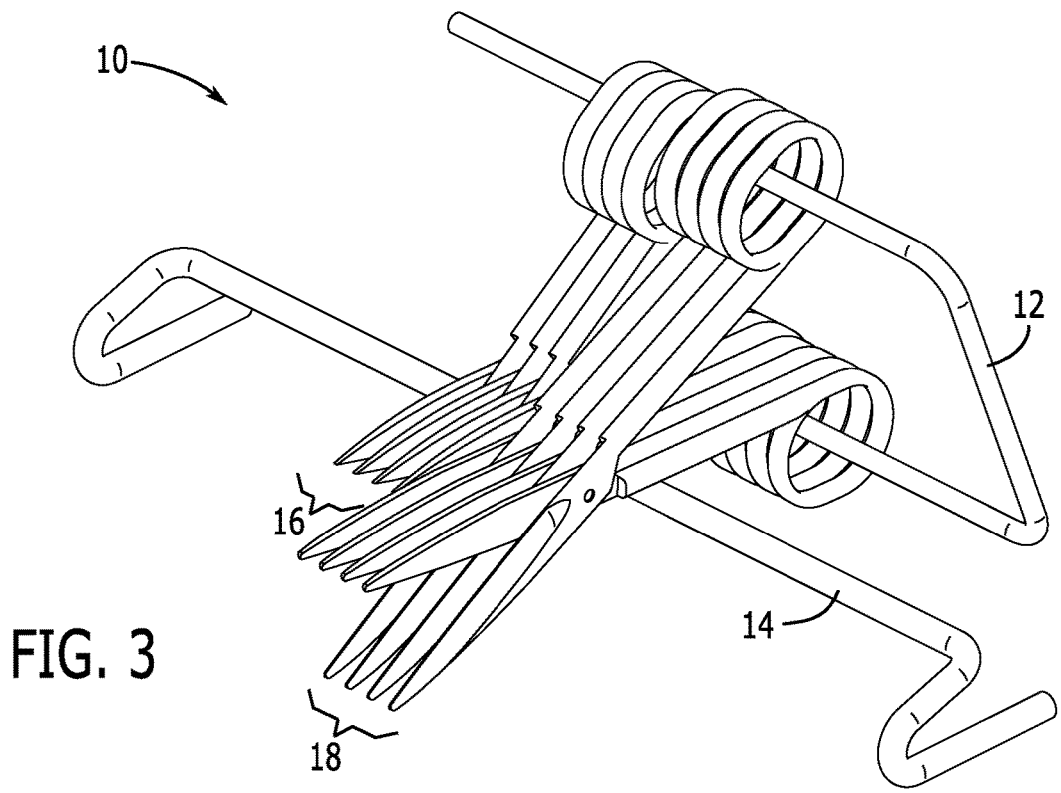
FIG. 3 conceptually illustrates another perspective view of the instrument bridge with the surgical instruments on the instrument stringer and the tips of the surgical instruments elevated by the instrument bridge.

In the following detailed description of the invention, numerous details, examples, and embodiments of the invention are described. However, it will be clear and apparent to one skilled in the art that the invention is not limited to the embodiments set forth and that the invention can be adapted for any of several applications.

Some embodiments provide a novel instrument bridge to elevate and protect the tips of both surgical instruments secured onto a sterilization/instrument stringer placed in a surgical instrument tray and surgical instruments loosely placed into the surgical instrument tray with the tips placed on the instrument bridge. In some embodiments, the instrument bridge provides a rigid stand that is configured to elevate and protect the tips of surgical instruments secured onto the sterilization/instrument stringer placed in the surgical instrument tray or loosely placed into the surgical instrument tray with their tips elevated and placed onto the instrument bridge. In some embodiments, the instrument bridge is manufactured in a plurality of different sizes that each fit different sized surgical instrument trays. In this way, there is nothing for the instruments to catch on, there is no lint residue or cross-contamination, and multiple sizes can accommodate most surgical instrument trays.

In some embodiments, the instrument bridge is a rigid medical instrument stand that is made of stainless steel. In some embodiments, the stainless steel instrument bridge is comprised of medical grade stainless steel, is reusable, works with all types and lengths of instruments, and can be sterilized. In some embodiments, the medical grade stainless steel comprises a particular medical grade stainless steel known as "304 stainless steel".

In some embodiments, the instrument bridge is a single-use medical instrument stand that is made of a plastic material. In some embodiments, the plastic single-use instrument bridge is comprised of medical grade plastic, is disposable, can be sterilized and works with all types and lengths of instruments. In some embodiments, the medical grade plastic material comprises one of ABS plastic and Teflon.

In some embodiments, the instrument bridge comprises an elongated instrument elevation bar and instrument bridge feet that are inseparably connected to the ends of the elongated instrument elevation bar, making a single component surgical instrument bridge. In some embodiments, the instrument bridge feet extend out from opposite ends of the elongated instrument elevation bar and raise the elongated instrument elevation bar above a surface platform in a horizontal orientation to stabilize the surgical instrument bridge when placed on the surface platform. In some embodiments, the elongated instrument elevation bar is configured to elevate a tip end of a surgical instrument. In some embodiments, the elongated instrument elevation bar is configured to elevate the tip end of the surgical instrument when an opposite end of the surgical instrument is secured by an instrument stringer. In some embodiments, the elongated instrument elevation bar is configured to elevate the tip end of the surgical instrument when the opposite end of the surgical instrument lays on (or touches) a surface of a surgical instrument tray. Different sizes of the surgical instrument bridge are fully supported and anticipated for use, as the surgical instrument bridge can be manufactured to satisfy any of several size requirements. In some embodiments, the surgical instrument bridge is approximately a size of the size of a surgical instrument tray on which the surgical instrument bridge is intended for use. In some embodiments, the surgical instrument bridge is approximately a size that is sufficient to support a particular type of surgical instrument. In some embodiments, the surgical instrument bridge is approximately a size that is sufficient to support a plurality of surgical instruments of different sizes.

In some embodiments, the particular type of surgical instrument comprises surgical scissors. However, other types of surgical instruments are supported by the surgical instrument bridge and, therefore, the particular type of surgical instrument is not limited to only surgical scissors. In some embodiments, the surgical instrument bridge elevates the tips of both small size surgical scissors and large sized surgical scissors. In some embodiments, the surgical instrument bridge is configured to elevate the tip ends of surgical scissors of any size. In some embodiments, finger holes at the handle end of the surgical scissors are looped onto an instrument stringer positioned nearby the surgical instrument bridge.

As stated above, the sharp and delicate tips of surgical instruments, when the instrument is secured onto a sterilization/instrument stringer and placed in a surgical instrument tray or loosely placed into the surgical instrument tray, can catch or hang up on the perforated bottom of the surgical instrument tray and break, bend or crack. To reduce the risk of damage by contact with the perforated bottom of the tray, cloth towels or other fabrics or materials are often used to elevate the instrument tips. However, the use of cloth towels or other fabrics or materials can result in lint or other fabric residue on the instruments. Furthermore, the instrument tips can catch on (or snag) the material and damage the tips. Embodiments of the instrument bridge to elevate and protect the tips of surgical instruments secured onto an instrument stringer placed in a surgical instrument tray or loosely placed into the surgical instrument tray with their tips elevated and placed onto the instrument bridge described in this specification solve such problems by providing a rigid instrument bridge (or stand) and placing the bridge/stand into the surgical instrument tray so that the distal ends (or tips) of surgical instruments which are secured onto a sterilization/instrument stringer are placed on top of the bridge/stand, or when the surgical instruments are loosely placed into the surgical instrument tray their tips are elevated by placement onto the instrument bridge, which itself is elevated, to prevent any or all of breaking, bending, and cracking of the tips on the perforated bottom of the surgical instrument tray.

In some embodiments, the instrument bridge is a rigid medical instrument stand that is made of medical grade stainless steel (e.g., 304 stainless steel or other medical grade stainless steel). In some embodiments, the instrument bridge is a single use device made of a medical grade plastic material (medical grade plastic material such as an ABS plastic material, Teflon, etc.). The instrument bridge protects the distal end of the surgical device from damage. To date, the instrument bridge is the only device that can raise the distal end of the surgical devices above the bottom of the surgical instrument tray while connected at the other end to the sterilization/instrument stringer or loosely placed in the tray.

Embodiments of the instrument bridge to elevate and protect the tips of surgical instruments secured onto an instrument stringer placed in a surgical instrument tray or loosely placed into the surgical instrument tray with their tips elevated and placed onto the instrument bridge described in this specification differ from and improve upon currently existing options. In particular, previous means of preventing damage to the tips of the surgical instruments includes placing a cloth towel or other material, often scrub uniforms, to elevate the tips in the surgical instrument tray. However, this is problematic in that the cloth towels or other material may not be clean which can result in cross-contamination during storage and transportation or may leave lint residue on and potentially damage instrument tips which catch on the material. By contrast, the instrument bridge of the present disclosure is comprised of stainless steel, is reusable, works with all types and lengths of instruments and can be sterilized. There is no lint residue or cross-contamination. There is nothing for the instruments to catch on and multiple sizes can accommodate most surgical instrument trays.

The instrument bridge to elevate and protect the tips of surgical instruments secured onto an instrument stringer placed in a surgical instrument tray or loosely placed into the surgical instrument tray with their tips elevated and placed onto the instrument bridge of the present disclosure may be comprised of the following elements. This list of possible constituent elements is intended to be exemplary only and it is not intended that this list be used to limit the instrument bridge of the present application to just these elements. Persons having ordinary skill in the art relevant to the present disclosure may understand there to be equivalent elements that may be substituted within the present disclosure without changing the essential function or operation of the instrument bridge.

1. Stainless steel re-usable stand designed as a single piece
2. Plastic stand designed for single-use stand The stainless steel stand is designed as a single piece that can be re-used with proper care and cleaning practices. The plastic stand is intended for single-use applications, and therefore, can be disposed of after use.

The instrument bridge to elevate and protect the tips of surgical instruments secured onto an instrument stringer placed in a surgical instrument tray or loosely placed into the surgical instrument tray with their tips elevated and placed onto the instrument bridge of the present disclosure generally works by selecting the appropriate size instrument bridge according to the size of the surgical instrument tray. Then positioning the correct size instrument bridge (either stainless steel or plastic version) into the surgical instrument tray with the feet on the bottom of the tray. Next would be placing the surgical instruments (which are secured onto a sterilization/instrument stringer) into the surgical instrument tray (or loosely placing the surgical instruments into the surgical instrument tray) and elevating the surgical instrument tips on the instrument bridge.

By way of example, FIG. 1 conceptually illustrates an exploded perspective view of a stand that elevates and protects surgical instruments 10. As shown in this figure, the overall stand includes an instrument stringer 12 and an instrument bridge 14. The instrument bridge 14 is designed to stand on its own. While the stringer 12 does not stand on its own, the stringer 12 is designed in a way that surgical instruments can be looped onto open-ended prongs of the stringer 12. The instrument bridge 14 is then oriented and positioned nearby the stringer 12 so as to elevate the tips of the surgical instruments on the stringer 12. This is demonstrated in the FIGS. 2-4, which are described below.

Specifically, FIG. 2 conceptually illustrates a left-side perspective view of the overall stand that elevates and protects surgical instruments 10 with the instrument bridge 14 placed nearby the stringer 12. Several surgical instruments are looped onto the stringer 12. In this example, the surgical instruments are surgical scissors of different sizes. In particular, the finger holes of several smaller sized surgical instruments 16 and several larger sized surgical instruments 18 are looped onto the instrument stringer 12 with the instrument bridge 14 positioned in a way that elevates the cutting blade tips of both the smaller sized surgical instruments 16 and the larger sized surgical instruments 18. At least for the smaller sized surgical instruments 16, the instrument bridge 14 shown in this figure is placed approximately at a pivot point of the smaller sized surgical instruments 16 (or specifically, scissors) with the cutting blades in an open configuration due to an open spread between the finger holes looped onto the prongs of the stringer 12. A right-side perspective view of the overall stand that elevates and protects surgical instruments 10 is illustrated in FIG. 3. From this right-side perspective view, the larger sized surgical instruments 18 are elevated by the instrument bridge 14 at a location along the scissors handle (or the shank, between the scissors pivot point and finger holes). The effect of positioning the instrument bridge 14 in this way is to elevate the tips of both the smaller sized surgical instruments 16 and the larger sized surgical instruments 18.

While the perspective views shown in FIGS. 2-3 clearly demonstrate how one may position the instrument bridge 14 and place the surgical instruments on the instrument bridge 14 to elevate their tips when the surgical instruments are looped onto the stringer 12, the view of the elevation between the surgical instrument tips and a bottom surface (such as a surgical tray) is not as shown as clearly. However, this is demonstrated in FIG. 4, which is described next.

Figure 4:
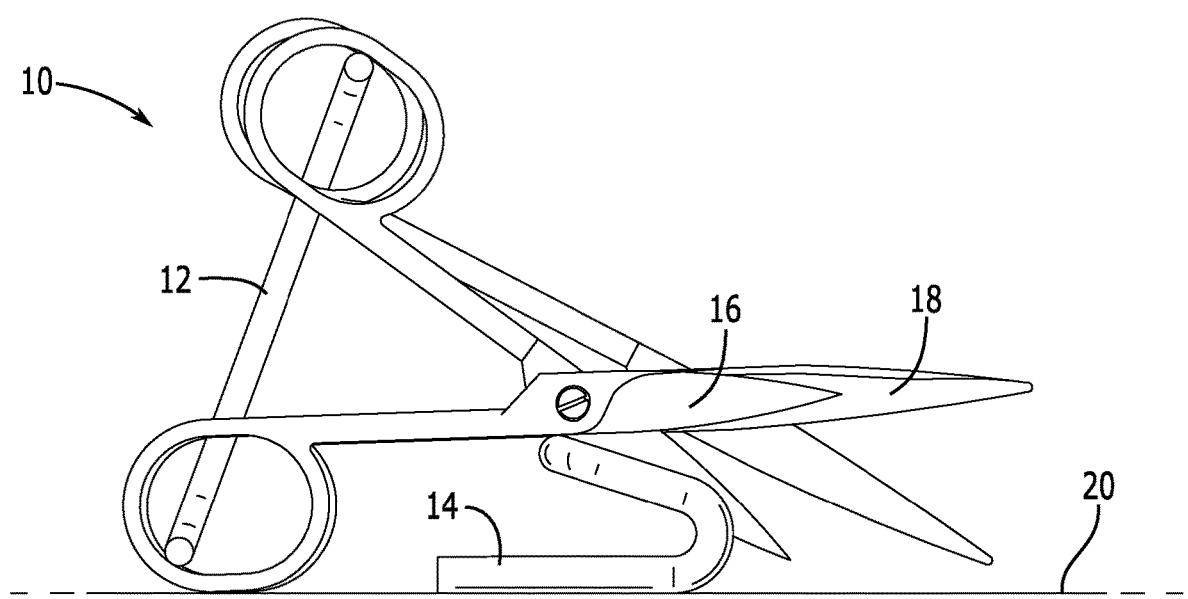
FIG. 4 conceptually illustrates a side elevation view of the instrument bridge in use to elevate the tips of the surgical instruments.

Specifically, FIG. 4 conceptually illustrates a side elevation view of the overall stand that elevates and protects surgical instruments 10 when used in a surgical tray 20. In particular, the instrument stringer 12 and the instrument bridge 14 are positioned in a way that elevates the tips of both the smaller sized surgical instruments 16 and the larger sized surgical instruments 18 above the surgical tray 20.

Although surgical scissors (or shears) are described, by reference to FIGS. 1-4, and shown for the surgical instruments, the instrument bridge of the present disclosure is designed to accommodate a multitude of other instruments. Therefore, the exemplary descriptions of scissors is not intended as limiting and a person of ordinary skill in the relevant art would appreciate the many different types of surgical instrumentation with tips or other parts that would be elevated above a surgical tray or other surface by utilization of the instrument bridge. Additionally, the above-described embodiments of the invention are presented for purposes of illustration and not of limitation. While these embodiments of the invention have been described with reference to numerous specific details, one of ordinary skill in the art will recognize that the invention can be embodied in other specific forms without departing from the spirit of the invention. Thus, one of ordinary skill in the art would understand that the invention is not to be limited by the foregoing illustrative details, but rather is to be defined by the appended claims.

I claim:

1. An instrument bridge stand to elevate and protect tips of surgical instruments comprising:
    an instrument stringer that is configured to secure a proximal end of a first surgical instrument by finger holes of the first surgical instrument that loop onto top and bottom bars of the instrument stringer, wherein the instrument stringer is configured to stand at a slanted orientation when the finger holes of the first surgical instrument are looped onto the top and bottom bars of the instrument stringer;
    an elongated instrument elevation bar that is configured to stand independently of the instrument stringer and elevate a distal end of the first surgical instrument in an elevated position; and
    instrument bridge feet that extend out from opposite ends of the elongated instrument elevation bar and raise the elongated instrument elevation bar above a surface platform in a horizontal orientation to stabilize the instrument stand while the elongated instrument elevation bar is standing independently of the instrument stringer.

2. The instrument stand of claim 1, wherein the elongated instrument elevation bar is configured to elevate a distal end of a second surgical instrument when a proximal end of the second surgical instrument lays on a surface of an instrument tray and is not secured by the instrument stringer.

3. The instrument stand of claim 1, wherein the elongated instrument elevation bar and the instrument bridge feet are inseparably connected as a surgical instrument bridge.

4. The instrument stand of claim 3, wherein the surgical instrument bridge is made out of a hard and rigid material.

5. The instrument stand of claim 4, wherein the hard and rigid material comprises medical grade stainless steel.

6. The instrument stand of claim 4, wherein the hard and rigid material comprises medical grade plastic.

7. The instrument stand of claim 3, wherein the surgical instrument bridge is approximately a size of a surgical instrument tray.

8. The instrument stand of claim 3, is configured to support a second surgical instrument thereon that is different from the first surgical instrument.

9. The instrument stand of claim 8, wherein the first surgical instrument comprises a pair of small size surgical scissors, wherein second surgical instrument comprises a pair of large size surgical scissors.

10. The instrument stand of claim 9, wherein the surgical instrument bridge is configured to elevate, above the surface platform, distal ends of both the pair of small size surgical scissors and the pair of large size surgical scissors.

11. The instrument stand of claim 10, wherein finger holes at proximal ends of both the pair of small size surgical scissors and the pair of large size surgical scissors are configured to be looped onto the top and bottom bars of the instrument stringer positioned in the slanted standing orientation nearby the surgical instrument bridge.

* * * * *